(12) United States Patent
Steiner et al.

(10) Patent No.: US 6,300,354 B1
(45) Date of Patent: Oct. 9, 2001

(54) N-SUBSTITUTED AZABICYCLOHEPTANE DERIVATIVES, PRODUCTION AND USE THEREOF

(75) Inventors: Gerd Steiner, Kirchheim; Thomas Höger, Edingen-Neckarhausen; Liliane Unger, Ludwigshafen; Hans-Jürgen Teschendorf, Dudenhofen; Frieder Juchelka, Leimen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/744,405

(22) PCT Filed: Jul. 20, 1999

(86) PCT No.: PCT/EP99/05164

§ 371 Date: Jan. 24, 2001

§ 102(e) Date: Jan. 24, 2001

(87) PCT Pub. No.: WO00/09501

PCT Pub. Date: Feb. 24, 2000

(30) Foreign Application Priority Data

Aug. 12, 1998 (DE) ................................................ 198 36 406

(51) Int. Cl.⁷ ........................ A61K 31/428; C07D 417/06
(52) U.S. Cl. ............................................. 514/373; 548/207
(58) Field of Search ............................. 548/207; 514/373

(56) References Cited

FOREIGN PATENT DOCUMENTS

| | | |
|---|---|---|
| 94/00431 | 1/1994 | (WO). |
| 94/00458 | 1/1994 | (WO). |
| 95/15312 | 6/1995 | (WO). |
| 96/04245 | 2/1996 | (WO). |
| 96/04272 | 2/1996 | (WO). |

OTHER PUBLICATIONS

Pharm.Tech.Thieme Verlag, Stgt 1978, Sucker et al.

Heterocycles, vol. 40, No. 1, 1995, Steiner319–330.

Chima (May 1990), 44, 120–123, No. 5.

*Primary Examiner*—Laura L. Stockton
(74) *Attorney, Agent, or Firm*—Keil & Weinkauf

(57) ABSTRACT

Compounds of the formula I:

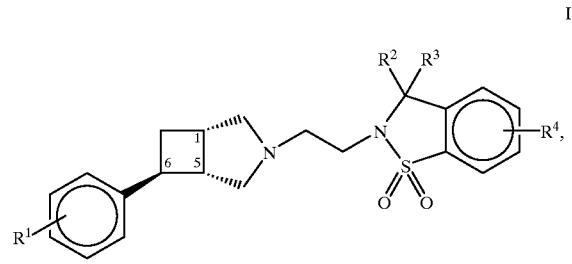

in which $R^1$, $R^2$, $R^3$ and $R^4$ have the meanings stated in the description, are described.

The novel compounds are suitable for controlling diseases.

2 Claims, No Drawings

N-SUBSTITUTED AZABICYCLOHEPTANE DERIVATIVES, PRODUCTION AND USE THEREOF

This application is a 371 of PCT/EP99/05164 filed Jul. 20, 1999.

The invention relates to novel N-substituted azabicycloheptane derivatives, their preparation and use for controlling diseases. Exo-6-phenyl-3-azabicyclo[3.2.0]heptane derivatives have interesting properties as potential neuroleptics (WO 94/00458, WO 95/15312). In this connection, the observed high affinities for $D_4$ and $5-HT_2$ receptors are particularly important.

The most interesting substance from the above classes of compounds with high $D_4/5-HT_{2A}$ affinity and good selectivity versus $D_2$ is (+)-(1S,5R,6S)-exo-3-[2-[6-(4-fluorophenyl)-3-azabicyclo-[3.2.0]heptan-3-yl]ethyl]-1H,3H-quinazoline-2,4-dione (=substance A), which represents a potential neuroleptic. However, there is an upper limit to the dosage of substance A owing to the prolongations occurring in the QT interval in the cardiac [sic] ECG.

Substances with better properties have now been found.

The invention relates to N-substituted 3-azabicyclo-[3.2.0]heptane derivatives of the formula I:

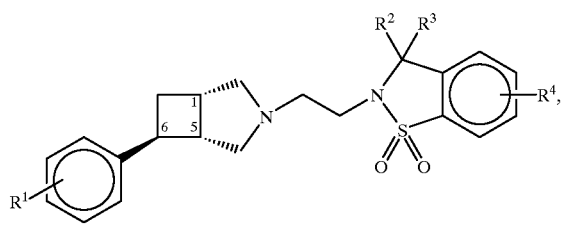

in which $R^1$ is fluorine or chlorine, $R^2$ and $R^3$ are hydrogen or $C_1$-$C_3$-alkyl, and $R^4$ is chlorine, methyl, nitro or amino, and the salts thereof with physiologically tolerated acids.

Preferred compounds are those in which $R^1$ is chlorine, preferably in the p position, $R^2$ is hydrogen or methyl, $R^3$ is hydrogen or methyl and $R^4$ is hydrogen.

The following compounds should be mentioned as particularly preferred:

(+)-(1S,5R,6S)-exo-2-[2-[6-(4-chlorophenyl)-3-azabicyclo-[3.2.0]heptan-3-yl]ethyl]-3,3-dimethyl-2,3-dihydro-1,2-benzisothiazole 1, 1-dioxide, (+)-(1S,5R,6S)-exo-2-[2-[6-(4-chlorophenyl)-3-azabicyclo-[3.2.0]heptan-3-yl]ethyl]-2,3-dihydro-1,2-benzisothiazole 1,1-dioxide, and (+)-(1S,5R,6S)-exo-2-[2-[6-(4-fluorophenyl)-3-azabicyclo-[3.2.0]-heptan-3-yl]-ethyl]-2,3-dihydro-1,2-benzisothiazole-1,1-dioxide.

The compounds of the formula I according to the invention can be prepared by reacting a compound of the formula II:

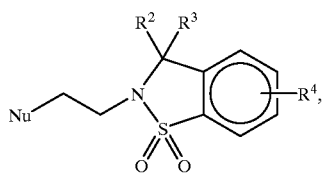

in which $R^2$, $R^3$ and $R^4$ have the abovementioned meanings, and Nu is a nucleofugic leaving group, with a 3-azabicyclo-[3.2.0]heptane derivative of the formula III as (+)-(1S,5R, exo-6S) enantiomer:

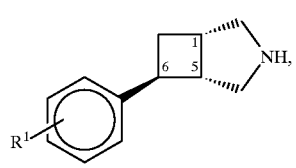

in which $R^1$ has the abovementioned meaning, and converting the compound obtained in this way where appropriate into the acid addition salt of a physiologically tolerated acid.

Halogen atoms, in particular bromine or chlorine, are suitable and preferred as nucleofugic leaving group for Nu.

The reaction is expediently carried out in the presence of an inert base such as triethylamine or potassium carbonate as acid acceptor in an inert solvent such as a cyclic saturated ether, in particular tetrahydrofuran or dioxane, or a benzenoid hydrocarbon such as toluene or xylene.

The reaction is generally carried out at temperatures from 20 to 150° C., in particular from 80 to 1400C., and is generally complete within 1 to 10 hours.

The compounds of the formula I according to the invention can be either recrystallized by recrystallization [sic] from conventional organic solvents, preferably from a lower alcohol such as ethanol, or purified by column chromatography.

The free 3-azabicyclo[3.2.0]heptane derivatives of the formula I can be converted in a conventional way into the acid addition salt of a pharmacologically suitable acid, preferably by treating a solution with one equivalent of the appropriate acid. Examples of pharmaceutically suitable acids are hydrochloric acid, phosphoric acid, sulfuric acid, methanesulfonic acid, sulfamic acid, maleic acid, fumaric acid, oxalic acid, tartaric acid or citric acid.

The compounds according to the invention have valuable pharmacological properties. They can be used as neuroleptics (in particular atypical), antidepressants, sedatives, hypnotics, CNS protectives or agents for treating cocaine dependency. It is possible for several of the types of action mentioned to occur in combination in a compound according to the invention.

The substances are characterized in particular by a very high and selective affinity for dopamine $D_4$ and serotonin 2A receptors.

The prolongations of the QT interval measured on the model of the guinea pig capillary muscle are negligibly small. The novel substances are therefore well tolerated even at high dosages.

The invention accordingly also relates to a therapeutic composition having a content of a compound of the formula I or its pharmacologically suitable acid addition salt as active ingredient in addition to conventional carriers and diluents, and to the use of the novel compounds for controlling diseases.

The compounds according to the invention can be administered orally or parenterally, intravenously or intramuscularly, in a conventional way.

The dosage depends on the age, condition and weight of the patient and on the mode of administration. As a rule, the daily dose of active ingredient is between about 1 and 100 mg/kg of body weight on oral administration and between 0.1 and 10 mg/kg of body weight on parenteral administration.

The novel compounds can be used in conventional solid or liquid pharmaceutical forms, e.g. as uncoated or (film-) coated tablets, capsules, powders, granules, suppositories, solutions, ointments, creams or sprays. These are produced in a conventional way. The active ingredients can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et. al.: Pharmazeutische Technologie, Thieme-Verlag, Stuttgart, 1978). The administration forms obtained in this way normally contain the active ingredient in an amount of from 1 to 99% by weight.

The substances of the formula II and III required as starting materials for synthesizing the compounds according to the invention are known, (WO 94/00458; Heterocycles 40 (1), 319–330 (1995), Chimia 1990, 44, 120) or can be synthesized from analogous starting materials by preparation methods described in the literature.

The following examples serve to illustrate the invention:

A Preparation of the Starting Materials a) 2,3-dihydro-1,2-benzoisothiazole 1,1-dioxide 25.3 g (138 mM [sic]) of saccharin were added in portions over the course of 90 min to 7.1 g (187 mM [sic]) of lithium aluminum hydride in 400 ml of absolute tetrahydrofuran with vigorous stirring under nitrogen; during this, the temperature was maintained at room temperature by cooling in ice. After stirring overnight, the mixture was cooled in an ice bath and, while stirring vigorously, water was cautiously added dropwise, followed by 10% strength sulfuric acid. After the precipitated hydroxides had been filtered off with suction, washing with THF, the filtrate was concentrated, the residue was partitioned between methylene chloride and water and, after acidifying with 10% strength sulfuric acid, the organic phase was washed thoroughly with sodium carbonate solution. The organic phase was dried with sodium sulfate and filtered and then concentrated. 12.0 g (52%) of product of adequate purity were isolated.

b) 3,3-Dimethyl-2,3-dihydro-1,2-benzoisothiazole 1,1-dioxide was prepared in a manner known from the literature (K.

Auer, E. Hungerbuhler, R. W. Lang Chimia 1990, 44, 120). 3,3-Diethyl-2,3-dihydro-1,2-benzoisothiazole 1,1-dioxide (m.p.: 174° C.), 3,3-dimethyl-6-nitro-2,3-dihydro-1,2-ben-zoisothiazole 1,1-dioxide (m.p.: 1870) and 3,3-dime-thyl-4-chloro-2,3-dihydro-1,2-benzisothiazole 1,1-dioxide were obtained analogously.

c) 2-(2-Chloroethyl)-3,3-dimethyl-2, 3-dihydro-1,2-benzoiso-thiazole 1,1-dioxide 2.1 g (32 mM [sic]) of 88% KOH powder and 250 mg of benzyltriethylammonium chloride were added to 2.5 g (12.7 mM [sic]) of 3,3-dimethyl-2,3-dihydro-1, 2-benzoisothiazole 1,1-dioxide in 50 ml of 1,2-dichloroethane, and the mixture was refluxed for 1 h. After cooling, the mixture was partitioned between ice-water and methylene chloride and, after making weakly acidic with hydrochloric acid, the organic phase was separated off. After the organic phase had been dried with sodium sulfate and concentrated, 3.2 g (97%) of product were isolated as an oil of adequate purity.

2-(2-Chloroethyl)-3,3-dimethyl-6-nitro-2,3-dihydro-1, 2-benzoisothiazole 1,1-dioxide, 2-(2-chloroethyl)-3, 3-diethyl-2,3-dihydro-1,2-benzoisothiazole 1,1-dioxide and 2-(2-chloroethyl)-4-chloro-3,3-dimethyl-2,3-dihydro-1, 2-benzoisothiazole 1,1-dioxide can be prepared in an analogous manner.

d) (+)-(1S,5R,6S)-Exo-6-(4-chlorophenyl)-3-azabicyclo-[3.2.0]heptane

The (+)-enantiomer was isolated by the method in Heterocycles 40 (1), 326 (1995).

e) (+)-(1S,5R,6S)-Exo-[3-(2-chloro) ethyl]-6-(4-chlorophenyl)-3-azabicyclo[3.2.0]heptane [sic]

7.3 g (50 mM [sic]) of 1-bromo-2-chloroethane and 3.5 g (25 mM [sic]) of finely powdered potassium carbonate were added to 10.0 g (48.2 mM [sic]) of (+)-(1S,5R,6S)-exo-6-(4-chlorophenyl)-3-azabicyclo[3.2.0]heptane in 200 ml of tetrahydrofuran, and the mixture was refluxed for 15 h. The mixture was then concentrated in a rotary evaporator, and the residue was taken up in 200 ml of methyl tert-butyl ether. The organic phase was washed with water at pH 10 and then the aqueous phase was back-extracted with methyl tert-butyl ether. The combined organic phases were dried with sodium sulfate and then concentrated. The crude product was purified by flash chromatography (silica gel, mobile phase ethyl acetate/n-heptane 1/1). 6.7 g (52%) of product were isolated as an oil with $[\alpha]_D$=+91.70 (EtOH).

(+)-(1S,5R,6S)-Exo-[3-(2-chloro)ethyl]-6-( 4-fluorophenyl)-3-azabicyclo[3.2.0]heptane [sic] was prepared in an analogous manner.

B Preparation of the Final Products

EXAMPLE 1

(+)-(1S,5R,6S)-Exo-2-[2-[6-( 4-chlorophenyl)-3-azabicyclo-[3.2.0]heptan-3-yl]ethyl ]-3,3-dimethyl-2,3-dihydro-1,2-benzoisothiazole 1,1-dioxide×HCl 3.75 g (14.5 mM [sic]) of 2-(2-chloroethyl )-3,3-dimethyl-2,3-dihydro-1,2-benzoisothiazole 1,1-dioxide and 2.0 g (14.5 mM [sic]) of finely powdered potassium carbonate were added to 3.0 g (14.5 mM [sic]) of (+)-(1S,5R, 6S)-exo-6-(4-chlorophenyl)-3-azabicyclo-[3.2.0]heptane in 60 ml of xylene, and the mixture was refluxed for 7 h. It was then concentrated in a rotary evaporator, and the residue was partitioned in water and methylene chloride at pH 10. The aqueous phase was extracted once more with methylene chloride, and then the combined organic phases were concentrated. The crude product was purified by column chromatography (silica gel, mobile phase methylene chloride/methanol 98/2. 4.2 g (69%) of product were isolated as an oil, which was dissolved in 200 ml of ether and converted with ethereal HCl into the hydrochloride (m.p. 230 to 232° C.). $[\alpha]_D$=+60.9° (EtOH)

Elemental analysis $C_{23}H_{27}N_2O_2SCl×HCl$; Calculated C, 59.10 H, 6.04 N, 5.99; Found C, 59.3 H, 6.3 N, 5.7.

EXAMPLE 2

(+)-(1S,5R,6S)-Exo-2-[2-[6-(4-chlorophenyl)-3-azabicyclo-[3.2.0]heptan-3-yl]ethyl]-2,3-dihydro-1, 2-benzoisothiazole 1,1-dioxide×HCl 360 mg (12.0 mM [sic]) of 80% sodium hydride were added to 2.0 g (11.8 mM [sic]) of 2,3-dihydro-1,2- benzoisothiazole 1,1-dioxide in 30 ml of DMF, and the mixture was stirred at a bath temperature of 90 to 100° C. for 2 h. After cooling, 3.2 g (11.8 mM [sic]) of (+)-(1S,5R,6S)-exo-[3-(2-chloro)ethyl]-6-(4-chlorophenyl)-3-azabicyclo[3.2.0]heptane were added, and the mixture was stirred at a bath temperature of 100° C. for 2 h. After cooling, the mixture was partitioned between methyl tert-butyl ether and water at pH 10, and the aqueous phase was extracted once more with methyl tert-butyl ether. The organic phases were combined and concentrated. The crude product was purified by column chromatography (silica gel, mobile phase methylene chloride/methanol 98/2). 4.5 g (95%) of product were isolated as an oil ([α]$_D$=+69.9°; EtOH) which was dissolved in 200 ml of ether and converted with ethereal HCl into the hydrochloride (m.p. 240 to 242° C.).

Elemental analysis $C_{21}H_{23}N_2O_2SCl\times HCl$; Calculated C, 57.40 H, 5.51 N, 6.38 Cl 16.14; Found C, 57.1 H, 5.5 N, 6.2 Cl 16.0.

The following were prepared in analogy to Example 1 and 2:

3. (+)-(1S,5R,6S)-Exo-2-[2-[6-4-fluorophenyl)-3-azabicyclo-[3.2.0]heptan-3-yl ]ethyl]-3,3-dimethyl-2,3-dihydro-1,2-ben-zoisothiazole 1,1-dioxide, m.p. 113 to 115° C.

4. (+)-(1S,5R,6S)-Exo-2-[2-[6-(4-fluorophenyl)-3-azabicyclo-[3.2.0]heptan-3-yl]ethyl]-3,3-diethyl-2,3-dihydro-1,2-benzoisothiazole 1,1-dioxide×HCl×H$_2$O, m.p. 77 to 79° C.

5. (+)-(1S,5R,6S)-Exo-2-[2-[6-(4-fluorophenyl)-3-azabicyclo-[3.2.0]heptan-3-yl]ethyl]-2,3-dihydro-1,2-benzoisothiazole 1,1-dioxide×HCl, m.p. 234 to 236° C., [α]$_D$=+67.1° (EtOH)

6. (+)-(1S,5R,6S)-Exo-2-[2-[6-(4-chlorophenyl)-3-azabicyclo-[3.2.0]heptan-3-yl3-ethyl ]-3,3-dimethyl-4-chloro-2,3-dihydro-1,2-benzisothiazole-1, 1-dioxide× HCl, m.p. 225 to 227° C.

We claim:

1. An N-substituted 3-azabicyclo[3.2.0]heptane derivative of the formula I:

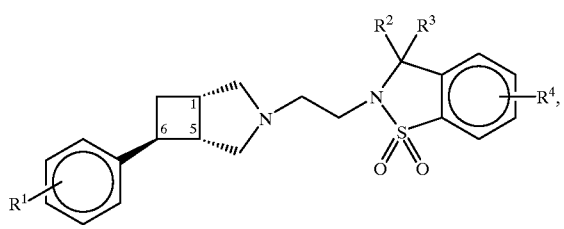

in which

R$^1$ is fluorine or chlorine,

R$^2$ and R$^3$ are hydrogen or C$_1$–C$_3$-alkyl, and

R$^4$ is chlorine, methyl, nitro or amino, and the salts thereof with physiologically tolerated acids.

2. A method for treating a neuroleptic disease which comprises administering to a host in need thereof a neuroleptically effective amount of a compound as defined in claim 1.

* * * * *